United States Patent [19]

Van Bakel et al.

[11] Patent Number: 5,281,598
[45] Date of Patent: Jan. 25, 1994

[54] PIPERAZINE DERIVATIVES

[75] Inventors: Franciscus H. A. Van Bakel, Uden; Gerhardus J. Heeres, Berghem; Ralf Plate, Oss; Johannes H. Wieringa, Bl Heesch, all of Netherlands

[73] Assignee: Akzo N.V., Arnhem, Netherlands

[21] Appl. No.: 44,526

[22] Filed: Apr. 9, 1993

[30] Foreign Application Priority Data

Apr. 13, 1992 [EP] European Pat. Off. ........ 92303266.8

[51] Int. Cl.$^5$ ................ A61K 31/495; C07D 295/088
[52] U.S. Cl. .................................... 514/255; 544/398; 544/403
[58] Field of Search ..................... 544/398; 514/255

[56] References Cited

FOREIGN PATENT DOCUMENTS 0365064 4/1990 European Pat. Off. .
837986 6/1960 United Kingdom .
962944 7/1964 United Kingdom .
09594 7/1991 World Int. Prop. O. .

*Primary Examiner*—Emily Bernhardt
*Attorney, Agent, or Firm*—William M. Blackstone

[57] ABSTRACT

The invention relates to a piperazine derivative having the formula

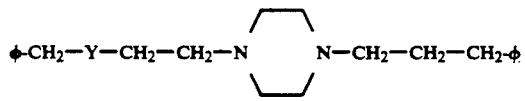

wherein each $\phi$ is a phenyl group which may independently be substituted by one or more substituents selected from the group consisting of lower alkyl, lower alkoxy, $CF_3$, and halogen, and Y is O or S, or a pharmaceutically acceptable salt thereof. The piperazine derivatives have sigma receptor affinity, and may be used for the treatment of psychosis.

5 Claims, No Drawings

PIPERAZINE DERIVATIVES

The invention relates to piperazine derivatives, the process for their preparation, as well as the use thereof for the manufacture of a medicament.

Piperazine derivatives are known in the art. Related piperazine derivatives are, for example, known from International patent application WO 91/09594. The most related compounds disclosed in this patent application are compound 46:

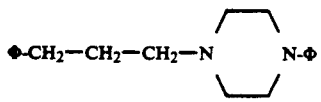

and compound 79:

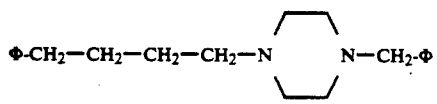

wherein $\Phi$ is phenyl, both displaying sigma receptor affinity and having potential utility in a range of therapeutic disorders including psychosis. It has been found that these compounds possess $\alpha_1$ adrenoceptor activity. It is generally known that $\alpha_1$ adrenoceptor antagonists show potent hypotensive effects (Goodman and Gilman's, The Pharmacological Basis of Therapeutics—Pergamon Press, 8th ed., p. 226 ff.). It is also known that many antipsychotic drugs induce (orthostatic) hypotension (see for instance C. A. Tamminga and J. Gerlach, Psychopharmacology: The Third Generation of Progress—Raven Press, p. 1129 ff.). The use of the neuroleptic drug clozapine is, because of the induction of orthostatic hypotension, seriously hampered (ibid., p. 1134). The sensitivity to this unwanted phenomenon increases further with increasing age (C. Salzman, ibid., p. 1167 ff.). To avoid this problem, especially in the elderly patients, there is a need for effective neuroleptic agents devoid of hypotensive side effects.

A solution to this problem is given in the present invention, which relates to psychotropic compounds having sigma receptor affinity devoid of $\alpha_1$ adrenoceptor activity, and which can find application as antipsychotic, anti-epilepsy, or anti-depressive drugs, or can be used to combat neuronal degenerative disorders and movement disorders such as dystonia and tardive dyskinesia.

The invention specifically relates to a piperazine derivative having the formula

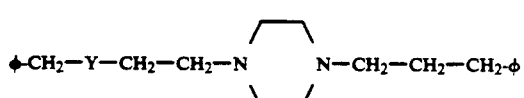

wherein each $\phi$ is a phenyl group which may independently be substituted by one or more substituents selected from the group consisting of lower alkyl, lower alkoxy, $CF_3$, and halogen, and Y is or S, or a pharmaceutically acceptable salt thereof.

A preferred compound according to the invention is the piperazine derivative according the formula I wherein both $\phi$ are unsubstituted phenyl groups. Most preferred is the piperazine derivative according the formula I wherein both $\phi$ are unsubstituted phenyl and Y is O.

In the definition of piperazine derivative I, the term lower alkyl means an alkyl group having preferably 1–6 carbon atoms, such as methyl, ethyl, propyl, isopropyl, butyl, isobutyl, tert-butyl, pentyl, and hexyl. More preferred are the alkyl groups having 1–4 carbon atoms, and most preferred is the methyl group.

The term lower alkoxy means an alkoxy group, the alkyl moiety of which has the same meaning as lower alkyl as defined previously. Preferred are alkoxy groups having 1–4 carbon atoms, and most preferred is the methoxy group. The term halogen means fluorine, chlorine, bromine or iodine. Fluorine and chlorine are preferred halogens.

The piperazine derivatives according to the invention can be prepared by methods known for the preparation of analogous piperazine derivatives.

A convenient method of preparation is the reduction of a carbonyl group in a derivative of the formula

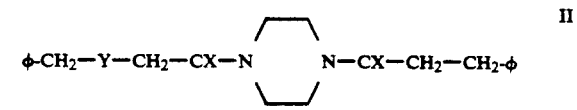

wherein $\phi$ has the previously defined meaning and X is O or $H_2$, with the proviso that at least one of the groups X is O, by treatment with a reagent which is suitable for the reduction of carbonyl groups, such as metal hydrides like lithium aluminium hydride and (di)borane.

Compounds of formula II can be prepared via various routes, for example:

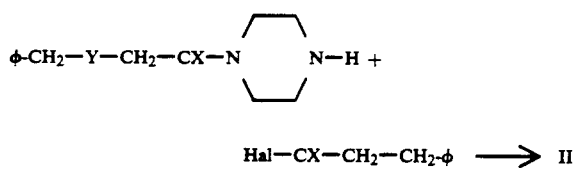

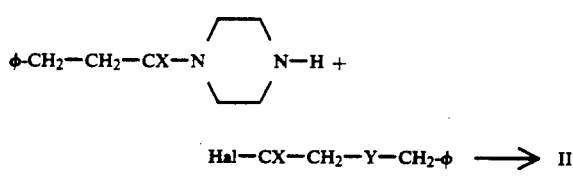

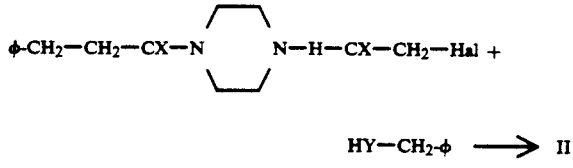

wherein $\phi$, X and Y have the previously defined meanings, and Hal is a halogen such as chlorine or bromine.

The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, $H_2SO_4$, $H_3PO_4$, acetic acid, propionic acid, glycolic acid, maleic acid, malonic acid, methanesulphonic acid, fumaric acid, succinic acid, tartaric acid, citric acid, benzoic acid, and ascorbic acid.

The compounds of the invention may be administered enterally or parenterally, and for humans preferably in a daily dosage of 0,001–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. a nasal spray. For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLE 1

1-[2-(phenylmethoxy)ethyl]-4-(3-phenylpropyl)piperazine dihydrochloride

To a stirred suspension of 4.0 g of sodium hydride (as a 60% dispersion in oil) in 40 ml of dry tetrahydrofuran (THF), was added dropwise under a nitrogen atmosphere a solution of 10.4 ml of benzyl alcohol in 60 ml of dry THF, and the mixture was stirred for 30 min. A solution of 29.5 g of 1-(chloroacetyl)-4-(3-phenylpropyl)piperazine in 110 ml of dry THF was added dropwise to this mixture and stirred for 20 h at room temperature. After work-up 29.5 g of the crude 1-(phenylmethoxyacetyl)-4-(3-phenylpropyl)piperazine in a mixture of 480 ml of dry diethyl ether and 95 ml of dry THF were added to a stirred suspension of 6.0 g of lithium aluminium hydride in 1 l of dry diethyl ether under a nitrogen atmosphere, at such a rate that the reaction temperature remained less than 10° C. The mixture was stirred for another 2.5 h at room temperature, the residual lithium aluminium hydride destroyed by addition of aqueous sodium hydroxide solution, the solid material filtered off, and the filtrate evaporated to dryness to give 24.5 g of an oil. This crude material was purified by silica chromatography, using a mixture of dichloromethane, methanol, and ammonium hydroxide as eluent to give 17.2 g of an oil. The oil was dissolved in 100 ml of diethyl ether and a saturated solution of hydrogen chloride in diethyl ether was added. The precipitate was filtered and recrystallised from methanol and diethyl ether to give 11.4 g of 1-[2-(phenylmethoxy)ethyl]-4-(3-phenylpropyl)piperazine dihydrochloride, m.p. 233° C.

EXAMPLE 2

In an analogous manner as described in Example 1 were prepared:
1-[3-(4-methylphenyl)propyl]-4-[2-(phenylmethoxy)ethyl]piperazine dihydrochloride, m.p. 238° C.

1-[2-[(4-chlorophenyl)methoxy]ethyl]-4-[3-(4-methylphenyl)propyl]piperazine dihydrochloride, m.p. 238° C.

1-[2-[(4-fluorophenyl)methoxy]ethyl]-4-[3-(4-methylphenyl)propyl]piperazine dihydrochloride, m.p. 238° C.

1-[3-(4-methylphenyl)propyl]-4-[2-[[3-(trifluoromethyl)phenyl]methoxy]ethyl]piperazine dihydrochloride, m.p. 221° C.

1-[2-[(4-chlorophenyl)methoxy]ethyl]-4-[3-(3-methoxyphenyl)propyl]piperazine dihydrochloride, m.p. 224° C.

EXAMPLE 3

1-[2-(phenylmethylthio)ethyl]-4-(3-phenylpropyl)piperazine dihydrochloride

To a stirred solution of 5.0 g of 1-(3-phenylpropyl)piperazine and 3.4 ml of triethylamine in 40 ml of toluene, under a nitrogen atmosphere, was added a solution of 5.02 g of (phenylmethylthio)acetyl chloride in 20 ml of toluene keeping the reaction temperature below 5° C. The reaction was continued for a further 45 min, and the mixture was poured into 40 ml of water. After work-up, 6.60 g of the purified [(phenylmethylthio)acetyl]-4-(3-phenylpropyl)piperazine in 100 ml of dry diethyl ether were added to a stirred suspension of 1.34 g of lithium aluminium hydride in 100 ml of dry diethyl ether under a nitrogen atmosphere, at such a rate as to maintain the reaction temperature below 5° C. The reaction was continued at this temperature for 30 min and the residual lithium aluminium hydride was destroyed by addition of an aqueous sodium hydroxide solution. The solid material was filtered, and the filtrate was evaporated to dryness to give 5.2 g of an oil, which was dissolved in 50 ml of diethyl ether after which a saturated solution of hydrogen chloride in diethyl ether was added. The precipitate was filtered and recrystallised to give 3.1 g of 1-[2-(phenylmethylthio)ethyl]-4-(3-phenylpropyl)piperazine dihydrochloride, m.p. 247° C.

EXAMPLE 4

The compound of Example 1 was prepared in an alternative manner:

a. To a stirred suspension of phenylpropionic acid (120 g) in toluene (120 ml) and pyridine (6 ml) was added thionyl chloride (115 ml), vigorous gassing ensued and the temperature fell rapidly to 5° C. Reaction was complete in 1 h and the solvent was evaporated in vacuo. The residue was redissolved in toluene (120 ml), the solution was filtered to remove pyridine hydrochloride and the filtrate was evaporated in vacuo to give 166 g of phenylpropionyl chloride.

b. Piperazine (110 g) was added rapidly to stirred acetic acid (1.1 l) resulting in a temperature rise to 45° C. After 1 h phenylpropionyl chloride (125 g) was added dropwise, allowing the temperature to rise to 35° C. After 3 h the mixture was filtered and the filtrate was evaporated in vacuo. The residue was acidified with hydrochloric acid solution and the neutral impurities were extracted with ethyl acetate. The aqueous layer was basified with 10N potassium hydroxide solution, saturated with sodium chloride, and extracted with ethyl acetate. After washing and evaporation 1-(3-phenylpropionyl)piperazine was obtained.

c. To a stirred solution of 1-(3-phenylpropionyl)piperazine (115 g) in toluene (557 ml) and triethylamine (76 ml) was added benzoyloxyacetyl chloride (87 ml) at such a rate to keep the temperature below 30° C. After 30 min water (577 ml) was added and the reaction was stirred for a further 30 min. The layers were separated and the organic layer was washed with sodium carbonate and sodium chloride solution. The dried solution was evaporated in vacuo to give 193 g of 1-[(phenylmethoxy)acetyl]-4-(3-phenylpropionyl)piperazine.

d. To a stirred solution of 1-[(phenylmethoxy)acetyl]-4-(3-phenylpropionyl)piperazine (193 g) in tetrahydrofuran (967 ml) under a nitrogen atmosphere, was added a molar solution of borane-tetrahydrofuran complex solution in tetrahydrofuran (2.4 l) and the mixture was refluxed for 1 h. The residual borane reagent was destroyed by dropwise addition of 5N hydrochloric acid solution (430 ml) and the tetrahydrofuran was removed by distillation. The cooled reaction mixture was basified with sodium hydroxide solution, the product was extracted with ethyl acetate, and the solvents were evaporated in vacuo, after which 1-[2-(phenylmethoxy)ethyl]-4-(3-phenylpropyl)piperazine (178 g) was obtained.

e. To a solution of 1-[2-(phenylmethoxy)ethyl]-4-(3-phenylpropyl)piperazine (178 g) in methanol (400 ml) was added a solution of hydrochloric acid in methanol (400 ml; 10%) and the solution was cooled and allowed to crystallise. The crystals were filtered, washed with methyl t-butylether/methanol 2:1 (150 ml) and dried under vacuum at 60° C. to give the hydrochloride salt (191 g), which was recrystallised from methanol to give 168 g of pure 1-[2-(phenylmethoxy)ethyl]-4-(3-phenylpropyl)piperazine dihydrochloride.

EXAMPLE 5

The compound of Example 1 was compared with the two most closely related prior art compounds, i.e. compounds 46 and 79 of WO 91/09594, with respect to their sigma receptor binding affinity and their $\alpha_1$ adrenoceptor affinity. The activities are expressed as pKi values ($-\log$ Ki values; Ki being the binding constant). The sigma receptor binding was assessed by the 1,3-di-o-tolylguanidine (DTG) binding as described by Fox et al., Eur. J. Pharmacol., 193, 139–143, 1991. The $\alpha_1$ adrenoceptor affinity was assessed by the prazosin (PRA) binding as described by de Boer et al., Arzneim. Forsch., 40, 550–554, 1990.

|  | PRA pKi | DTG pKi |
|---|---|---|
| Compound of Example 1 | 5.7 | 8.7 |
| Compound 46 of WO 91/09594 | 8.7 | 8.2 |
| Compound 79 of WO 91/09594 | 7.4 | 8.6 |

The compound of this invention exhibits similar activity as sigma ligand, whereas the unwanted $\alpha_1$ adrenoceptor affinity is about 50 to 1000 times less than for the prior art compounds.

We claim:

1. A piperazine derivative having the formula

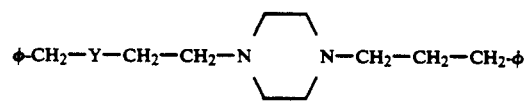

wherein each $\phi$ is a phenyl group which may independently be substituted by one or more substituents selected from the group consisting of lower alkyl, lower alkoxy, $CF_3$, and halogen, and Y is O or S, or a pharmaceutically acceptable salt thereof.

2. The piperazine derivative of claim 1 wherein each $\phi$ is an unsubstituted phenyl group.

3. The piperazine derivative of claim 1 wherein each $\phi$ is an unsubstituted phenyl group and Y is O.

4. A pharmaceutical composition comprising an effective amount of the piperazine derivative of claim 1 for treating psychosis and a pharmaceutically suitable auxiliary.

5. A method for treating psychosis comprising administering an effective amount of a piperazine derivative according to claim 1.

* * * * *